(12) United States Patent
Bander

(10) Patent No.: US 12,285,503 B2
(45) Date of Patent: *Apr. 29, 2025

(54) METHODS AND REAGENTS FOR TUMOR TARGETING WITH GREATER EFFICACY AND LESS TOXICITY

(71) Applicant: CORNELL UNIVERSITY, Ithaca, NY (US)

(72) Inventor: Neil H. Bander, Chappaqua, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 87 days.

This patent is subject to a terminal disclaimer.

(21) Appl. No.: 18/363,369

(22) Filed: Aug. 1, 2023

(65) Prior Publication Data

US 2024/0000980 A1   Jan. 4, 2024

Related U.S. Application Data

(63) Continuation of application No. 17/198,574, filed on Mar. 11, 2021, now Pat. No. 11,738,101, which is a continuation of application No. 16/610,816, filed as application No. PCT/US2018/030620 on May 2, 2018, now Pat. No. 11,491,247.

(60) Provisional application No. 62/500,187, filed on May 2, 2017.

(51) Int. Cl.
*A61K 51/10* (2006.01)
*A61K 51/04* (2006.01)
*A61P 35/00* (2006.01)

(52) U.S. Cl.
CPC ...... *A61K 51/1072* (2013.01); *A61K 51/0402* (2013.01); *A61P 35/00* (2018.01)

(58) Field of Classification Search
CPC .......... A61K 51/04; A61K 51/10; A61P 35/00
See application file for complete search history.

(56) References Cited

U.S. PATENT DOCUMENTS

| | | | |
|---|---|---|---|
| 6,683,162 B2 | 1/2004 | Scheinberg et al. | |
| 7,011,812 B1 | 3/2006 | Griffiths et al. | |
| 7,514,078 B2 * | 4/2009 | Bander ................. | C07K 16/30 424/179.1 |
| 7,666,414 B2 | 2/2010 | Bander | |
| 8,778,305 B2 | 7/2014 | Pomper et al. | |
| 8,889,631 B2 | 11/2014 | Peterson | |
| 8,926,944 B2 | 1/2015 | Babich et al. | |
| 9,223,981 B2 | 12/2015 | Itani | |
| 9,289,519 B2 | 3/2016 | Scheinberg et al. | |
| 9,364,554 B2 | 6/2016 | Hutchinson et al. | |
| 9,388,144 B2 | 7/2016 | Babich et al. | |
| 9,574,006 B2 | 2/2017 | Lazar et al. | |
| 9,694,091 B2 | 7/2017 | Pomper et al. | |
| 9,776,977 B2 | 10/2017 | Pomper et al. | |
| 9,789,195 B2 | 10/2017 | Cheng et al. | |
| 10,179,117 B2 | 1/2019 | Babich et al. | |
| 10,603,276 B2 | 3/2020 | Fahmy et al. | |
| 10,980,901 B2 | 4/2021 | Morgenstern et al. | |
| 11,059,903 B2 | 7/2021 | Holgate et al. | |
| 11,491,247 B2 | 11/2022 | Bander | |
| 11,738,101 B2 | 8/2023 | Bander | |
| 2003/0138432 A1 | 7/2003 | Glazier | |
| 2006/0088539 A1 | 4/2006 | Bander | |
| 2012/0322672 A1 | 12/2012 | Hua et al. | |
| 2015/0110814 A1 | 4/2015 | Olson et al. | |
| 2015/0148294 A1 | 5/2015 | Marks et al. | |
| 2015/0190529 A1 | 7/2015 | Peterson et al. | |
| 2015/0232560 A1 | 8/2015 | Heindl et al. | |
| 2016/0228587 A1 | 8/2016 | Eder et al. | |
| 2016/0256579 A1 | 9/2016 | Shalom | |
| 2017/0002076 A1 | 1/2017 | Kim et al. | |
| 2017/0014528 A1 | 1/2017 | Sengupta et al. | |
| 2017/0037142 A1 | 2/2017 | Bander | |
| 2017/0081298 A1 | 3/2017 | Ray et al. | |
| 2017/0189568 A1 | 7/2017 | Kung et al. | |
| 2017/0246327 A1 | 8/2017 | Kopka et al. | |
| 2018/0051039 A1 | 2/2018 | Pomper et al. | |

(Continued)

FOREIGN PATENT DOCUMENTS

| | | |
|---|---|---|
| WO | 00/53236 A2 | 9/2000 |
| WO | 02/098897 A2 | 12/2002 |

(Continued)

OTHER PUBLICATIONS

Kristell L.S. Chatlic et al. Towards Personalized Treatment of Prostate Cancer: PSMA I&T, a promising Prostate-Specific Membrane Antigen-Targeted Theranostic Agent, Theranostics, 6(6), 849-861. (Year: 2016).*
Office Action in U.S. Appl. No. 17/198,574 (mailed Oct. 20, 2021).
Office Action in U.S. Appl. No. 17/198,574 (mailed Jun. 10, 2021).
Office Action in U.S. Appl. No. 17/198,574 (mailed Jul. 11, 2022).
International Search Report and Written Opinion for International Application No. PCT/US2024/024363 (mailed Jul. 2, 2024).
Kratochwil et al., "Targeted α-Therapy of Metastatic Castration-Resistant Prostate Cancer with 225Ac-PSMA-617: Dosimetry Estimate and Empiric Dose Finding," J. Nuclear Medicine 58:1624-1631 (2017).

(Continued)

*Primary Examiner* — Johann R Richter
*Assistant Examiner* — Jagadishwar R Samala
(74) *Attorney, Agent, or Firm* — Troutman Pepper Locke LLP (Rochester)

(57) ABSTRACT

The present invention relates to a method for treating cancer. This method involves providing a first agent comprising a first targeting component coupled to a first cancer therapeutic component and providing a second agent comprising a second targeting component coupled to a second cancer therapeutic component. The first and second targeting components have different biodistributions and/or pharmacokinetics. The first and second agents are administered to a subject having cancer to treat the cancer. Also disclosed is a combination therapeutic comprising the first and second agents.

19 Claims, 9 Drawing Sheets

(56) References Cited

U.S. PATENT DOCUMENTS

| | | |
|---|---|---|
| 2018/0085478 A1 | 3/2018 | Pomper et al. |
| 2018/0104353 A1 | 4/2018 | Sengupta et al. |
| 2018/0148514 A1 | 5/2018 | Williams |
| 2020/0281955 A1 | 9/2020 | Xu et al. |
| 2020/0339625 A1 | 10/2020 | Lin et al. |
| 2021/0154338 A1 | 5/2021 | Bander |
| 2021/0196844 A1 | 7/2021 | Bander |
| 2022/0081401 A1 | 3/2022 | Narayanan et al. |
| 2023/0364271 A1 | 11/2023 | Bander |
| 2024/0000979 A1 | 1/2024 | Bander |

FOREIGN PATENT DOCUMENTS

| | | |
|---|---|---|
| WO | 2003/024388 A2 | 3/2003 |
| WO | 2005070456 A2 | 8/2005 |
| WO | 2011108955 A1 | 9/2011 |
| WO | 2013/009475 A1 | 1/2013 |
| WO | 2015/057250 A1 | 4/2015 |
| WO | 2016/123591 A2 | 8/2016 |
| WO | 2017/165473 A1 | 9/2017 |
| WO | 2018204477 A1 | 11/2018 |
| WO | 2020/126064 A1 | 6/2020 |
| WO | 2022072293 A2 | 4/2022 |

OTHER PUBLICATIONS

Sharkey R. M. et al., "Combination Radioimmunotherapy and Chemoimmunotherapy Involving Different or the Same Targets Improves Therapy of Human Pancreatic Carcinoma Xenograft Models," Molecular Cancer Therapeutics, 10(6):1072-1081 (2011).
International Search Report and Written Opinion of the International Searching Authority for International Application No. PCT/US18/30620, mailed Jul. 13, 2018.
Papademetriou I. T. et al., "In Vivo Performance of Polymer Nanocarriers Dually-Targeted to Epitopes of the Same or Different Receptors," Biomaterials, 34(13): 3459-3466 (2013).
Extended European Search Report and Opinion for European Application No. 18794018.4 (dated Dec. 21, 2020).
Niaz et al., "PD16-11 Comparison of Prostate-Specific Membrane Antigen (PSMA)—Targeted Radionuclide Therapy (TRT) with Lutetium-177 LU)-L-177) via Antibody, J591 vs. Small Molecule Ligand PSMA-617", The Journal of Urology; Annual Meeting of The American-Urological-Association (AUA) 203(4):E367 (2020).
Gerber et al., "Combining Antibody-Drug Conjugates and Immune-Mediated Cancer Therapy: What to Expect?," Biochemical Pharmacology 102:1-6 (2015).
Mugra et al., "Synergistic Co-Targeting of Prostate-Specific Membrane Antigen and Androgen Receptor in Prostate Cancer," The Prostate 75(3):242-254 (2014).
Kiess et al., "Prostate-Specific Membrane Antigen as a Target for Cancer Imaging and Therapy," Q J Nucl Med Mol Imaging 59(3):241-268 (2015).
Bander et al., "Phase 1 Clinical Trial Targeting a monoclonal Antibody (MAB) to the Extracellular Domain of Prostate Specific Membrane Antigen (PSMAEXT) in Hormone-Independent Patients," Journal of Urology 163(4):160 (2000).
Bander et al., "Targeting Metastatic Prostate Cancer with Radiolabeled Monoclonal Antibody J591 to the Extracellular Domain of Prostate Specific Membrane Antigen," J. Urology 170:1717-1721 (2003).
Smith-Jones et al., "In Vitro Characterization of Radiolabeled Monoclonal Antibodies Specific for the Extracellular Domain of Prostate-Specific Membrane Antigen," Cancer Res. 60(18):5237-5243 (2000).
Bander et al., "Phase I Trial of 177Lutetium-Labeled J591, a Monoclonal Antibody to Prostate-Specific Membrane Antigen, in Patients With Androgen-Independent Prostate Cancer," J. Clin. Oncol. 23(21):4591-4601 (2005).
Kudgus, et al., "Tuning Pharmacokinetics and Biodistribution of a Targeted Drug Delivery System Through Incorporation of a Passive Targeting Component," Scientific Reports, 4:5669 (1-9) (2014).

Office Action in U.S. Appl. No. 16/610,816 (mailed Oct. 5, 2021).
Office Action in Japan Application No. 2019-560384 (issued Dec. 20, 2021).
Kratochwil et al., "PSMA-Targeted Radionuclide Therapy of Metastatic Castration-Resistant Prostate Cancer with 177Lu-Labeled PSMA-617," J. Nucl. Med. 57(8):1170-1176 (2016).
Restriction Requirement in U.S. Appl. No. 16/610,816 (mailed Apr. 29, 2021).
Kratochwil et al., "Targeted Alpha Therapy of mCRPC: Dosimetry Estimate of 213Bismuth-PSMA-617," Eur. J. Nucl. Med. Mol. Imaging 45:31-37 (2018).
Sartor et al., "Lutetium-177-PSMA-617 for Metastatic Castration-Resistant Prostate Cancer," N. Engl. J. Med. 385 (12):1091-1103 (2021) [Author Manuscript].
Kabasakal et al., "Pre-Therapeutic Dosimetry of Normal Organs and Tissues of 177Lu-PSMA-617 Prostate-Specific Membrane Antigen (PSMA) Inhibitor in Patients with Castration-Resistant Prostate Cancer," Eur. J. Nucl. Med. Mol. Imaging 42:1976-1983 (2015).
NCRP, "Misadministration of Radioactive Material in Medicine—Scientific Background," NCRP Commentary No. 7, Chapter 4: p. 27 (1991).
Bodei et al., "Long-Term Evaluation of Renal Toxicity After Peptide Receptor Radionuclide Therapy with 90Y-Dotatoc and 177Lu-Dotatate: The Role of Associated Risk Factors," Eur. J. Nucl. Med. Mol. Imaging 35:1847-1856 (2008).
Delker et al., "Dosimetry for 177Lu-DKFZ-PSMA-617: A New Radiopharmaceutical for the Treatment of Metastatic Prostate Cancer," Eur. J. Nucl. Med. Mol. Imaging 43:42-51 (2016).
Emami et al., "Tolerance of Normal Tissue to Therapeutic Irradiation," Int. J. Radiation Oncol. Biol. Phys. 21(1): 109-122 (1991).
Fendler, et al., "Preliminary Experience with Dosimetry, Response and Patient Reported Outcome After 177Lu-PSMA-617 Therapy for Metastatic Castration-Resistant Prostate Cancer," Oncotarget 8(2):3581-3590 (2017).
Okamoto et al., "Radiation Dosimetry for 177Lu-PSMA I&T in Metastatic Castration-Resistant Prostate Cancer: Absorbed Dose in Normal Organs and Tumor Lesions," J. Nucl. Med. 58(3):445-450 (2017).
Gleisner et al., "EANM Dosimetry Committee Recommendations for Dosimetry of 177Lu-labelled Somatostatin-Receptor- and PSMA-Targeting Ligands," Eur. J. Nucl. Med. Mol. Imaging (2022), 49:1778-1809.
Deasy et al., "Radiotherapy Dose-vol. Effects on Salivary Gland Function," Int. J. Radiat. Oncol. Biol. Phys. 76(3 Suppl):S58-63 (2010) [Author Manuscript].
Paganelli et al., "Dosimetry and Safety of 177Lu PSMA-617 along with Polyglutamate Parotid Gland Protector: Preliminary Results in Metastatic Castration-Resistant Prostate Cancer Patients," Eur. J. Nucl. Med. Mol. Imaging 47 (13):3008-3017 (2020).
Afshar-Oromieh et al., "The Diagnostic Value of PET/CT Imaging with the 68Ga-Labelled PSMA Ligand HBED-CC in the Diagnosis of Recurrent Prostate Cancer," Eur. J. Nucl. Med. Mol. Imaging 42:197-209 (2015).
Afshar-Oromieh et al., "Repeated PSMA-Targeting Radioligand Therapy of Metastatic Prostate Cancer with 131I-MIP-1095," Eur. J. Nucl. Med. Mol. Imaging 44:950-959 (2017).
Van Kalmthout et al., "Impact of External Cooling with Icepacks on 68Ga-PSMA Uptake in Salivary Glands," EJNMMI Res. 8:56 (2018).
Yilmaz et al., "Effect of External Cooling on 177Lu-PSMA Uptake by the Parotid Glands," J. Nucl. Med. 60:1388-1393 (2019).
National Cancer Institute, "Radiation Therapy to Treat Cancer", accessed at www.cancer.gov/about-cancer/treatment/types/radiation-therapy.
Gale, R.P., "Combination Cancer Therapy," Merck Manual Consumer Version accessed at: https://www.merckmanuals.com/home/cancer/prevention-and-treatment-of-cancer/combination-cancer-therapy.
Al-Lazikani et al., "Combinatorial Drug Therapy for Cancer in the Post-Genomic Era," Nat. Biotechnol. 30(7):679-692 (2012).

(56) References Cited

OTHER PUBLICATIONS

"How is Chemotherapy Used to Treat Cancer," American Cancer Society accessed at: https://www.cancer.org/treatment/treatments-and-side-effects/treatment-types/chemotherapy/how-is-chemotherapy-used-to-treat-cancer.html.

ClinicalTrials.gov Identifier NCT04886986 accessed at: https://clinicaltrials.gov/ct2/show/NCT04886986.

Sarnelli et al., "Dosimetry of 177Lu-PSMA-617 after Mannitol Infusion and Glutamate Tablet Administration: Preliminary Results of EUDRACT/RSO 2016-002732-32 IRST Protocol," Molecules 24:621 (2019).

Vallabhajosula et al., "Pharmacokinetics and Biodistribution of 111In- and 177Lu-Labeled J591 Antibody Specific for Prostate-Specific Membrane Antigen: Prediction of 90Y-J591 Radiation Dosimetry Based on 111In or 177Lu?," J. Nucl. Med. 46(4):634-641 (2005).

Pandit-Taskar et al., "89Zr-huJ591 Immuno-PET Imaging in Patients with Advanced Metastatic Prostate Cancer," Eur. J. Nucl. Med. Mol. Imaging 41(11):2093-2105 (2014) [Author Manuscript].

Haberkorn et al., "New Strategies in Prostate Cancer: Prostate-Specific Membrane Antigen (PSMA) Ligands for Diagnosis and Therapy," Clin. Cancer Res. 22(1):9-15 (2016).

Lütje et al., "PSMA Ligands for Radionuclide Imaging and Therapy of Prostate Cancer: Clinical Status," Theranostics 5 (12):1388-1401 (2015).

Tagawa et al., "Anti-Prostate-Specific Membrane Antigen-Based Radioimmunotherapy for Prostate Cancer," Cancer 116(4 Suppl):1075-1083 (2010).

Zechman et al., "Radiation Dosimetry and First Therapy Results with a 124I/ 131I-Labeled Small Molecule (MIP-1095) Targeting PSMA for Prostate Cancer Therapy," Eur. J. Nucl. Med. Mol. Imaging 41:1280-1292 (2014).

Notice of Reasons for Rejection in Japan Patent Application No. 2019-560384 (mailed Sep. 1, 2022).

International Search Report and Written Opinion for International Application No. PCT/US21/52269 (mailed Feb. 3, 2022).

International Search Report and Written Opinion for International Application No. PCT/US21/52271 (mailed May 12, 2022).

Third Notice of Reasons for Rejection in Japanese Patent Application No. 2019-560384, mailed Apr. 26, 2023.

Kristell L.S. Chatalic et al., "Towards Personalized Treatment of Prostate Cancer: PSMA I&T, a Promising Prostate-Specific Membrane Antigen-Targeted Theranostic Agent," Theranostics 6(6):849-861 (2016).

* cited by examiner

Intercalated ducts; 20x

Intercalated ducts; 10x

A

4x

B

10x

A  B

METHODS AND REAGENTS FOR TUMOR TARGETING WITH GREATER EFFICACY AND LESS TOXICITY

This application is a continuation of U.S. Patent Application Ser. No. 17/198,574, filed Mar. 11, 2021, which is a continuation of U.S. patent application Ser. No. 16/610,816, filed Nov. 4, 2019, now U.S. Pat. No. 11,491,247, issued Nov. 8, 2022, which is a national stage application under 35 U.S.C. § 371 of International Patent Application No. PCT/US2018/030620, filed May 2, 2018, which claims the benefit of U.S. Provisional Patent Application Ser. No. 62/500,187, filed May 2, 2017, which is hereby incorporated by reference in its entirety.

FIELD OF THE INVENTION

The present invention relates to methods and reagents for tumor targeting with greater therapeutic efficacy and less toxicity.

BACKGROUND OF THE INVENTION

Combination therapy is a common, accepted treatment approach for virtually all types of cancers and has been the standard therapeutic approach for several decades. The basis for the adoption of combination therapy was the early chemotherapy experience where it was determined that the high mutational rate of cancers allowed rapid development of resistant strains of tumor cells when only a single agent was employed. The goal of combination therapies is to increase efficacy and minimize the development of tumor resistance or escape. This is generally achieved by employing 2 or more anti-cancer agents each of which has a different mechanism of action, making the development of resistant tumor cells more difficult and less likely. The additive or synergistic effects of combining two or more agents can be the difference between successful and unsuccessful treatment of the patient.

Many combination treatment regimens are well known in the oncology field. As an example, MOPP (an acronym for mechlorethamine, vincristine, procarbazine, prednisone) is a curative treatment regimen for Hodgkins' Disease. Several different combination regimens (which all include cisplatin, vinblastine, and bleomycin) are accepted in the treatment of testicular cancer, which is curable in up to 98% of diagnosed cases. In all, more than 300 different combination regimens have been used.

The main drawback to combination therapy is often that it also results in an increase in toxicity. For example, most forms of nonsurgical cancer therapy, such as external irradiation and chemotherapy, are limited in their efficacy because of toxic side effects to normal tissues and cells as well as the limited specificity of these treatment modalities for cancer cells. This limitation is also of importance when anti-cancer antibodies are used for targeting toxic agents, such as isotopes, drugs, and toxins, to cancer sites, because, as systemic agents, they also circulate to sensitive cellular compartments such as the bone marrow. In acute radiation injury, there is destruction of lymphoid and hematopoietic compartments as a major factor in the development of septicemia and subsequent death. Thus, methods of reducing the toxic effects of cancer therapy while maintaining or even increasing efficacy are in high demand.

The present invention is directed to overcoming these and other deficiencies in the art.

SUMMARY OF THE INVENTION

The present invention relates to a method of treating cancer. This method involves providing a first agent comprising a first targeting component coupled to a first cancer therapeutic component and providing a second agent comprising a second targeting component coupled to a second cancer therapeutic component. The first and second targeting components have different biodistributions and/or pharmacokinetics. The first and second agents are then administered, to a subject having cancer, to treat the cancer.

The present invention also pertains to a combination therapeutic for treating cancer. The combination therapeutic includes a first agent comprising a first targeting component coupled to a first cancer therapeutic component and a second agent comprising a second targeting component coupled to a second cancer therapeutic component. The first and second targeting components have different biodistributions and/or pharmacokinetics.

The present invention has devised a way to overcome the MTD of a targeted agent in order to achieve improved efficacy with no increase in, and an opportunity to decrease, its toxicity. The present invention proposes the use of two individual targeting agents, rather than one, each targeting the same molecule or cell type. In this approach, each of the two targeted agents has a different biodistribution and/or pharmacokinetics from the other. Importantly, the different biodistributions and pharmacokinetics of these respective agents results in differing, non-overlapping toxicities of each of the two respective targeted agents. When the two targeted agents are combined in a treatment strategy, the result is that both drugs converge, simultaneously or sequentially, at the desired target site thereby providing a combined treatment effect. The normal tissue toxicity, however, is not increased as the biodistribution of the two targeted agents differs such that there is no increase in drug delivery to the normal tissues and, therefore, no increase in toxicity.

BRIEF DESCRIPTION OF THE DRAWINGS

FIG. 1A shows $^{177}$Lu internalization in LNCaP cells. FIG. 1B shows $^{177}$Lu internalization in CWR22Rv1 cells.

DETAILED DESCRIPTION OF THE INVENTION

Figure 1A:
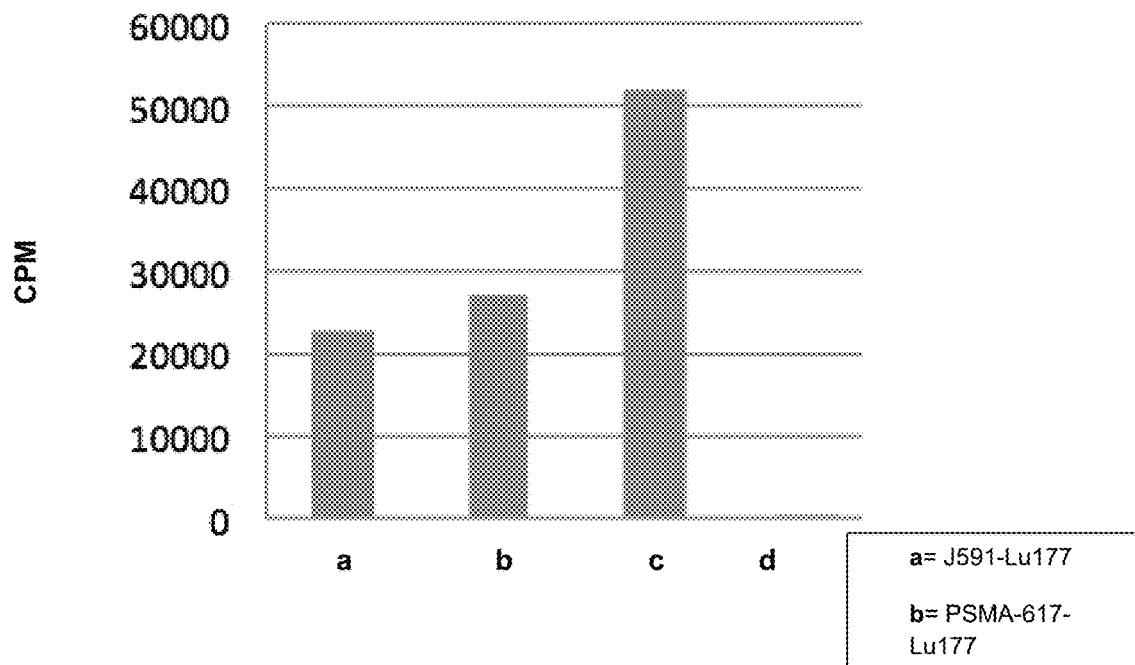
FIGS. 1A-1B show that co-incubation of radiolabeled anti-PSMA antibody J591-$^{177}$Lu and radiolabeled PSMA-617-$^{177}$Lu (a small molecule PSMA inhibitor) results in additive $^{177}$Lu internalization in PSMA-positive cells in vitro.

The present invention relates to a method of treating cancer. This method involves providing a first agent comprising a first targeting component coupled to a first cancer therapeutic component and providing a second agent comprising a second targeting component coupled to a second cancer therapeutic component. The first and second targeting components have different biodistributions and/or pharmacokinetics. The first and second agents are then administered, to a subject having cancer, to treat the cancer.

As used herein, the term "treat" refers to the application or administration of the first and second agents of the invention to a subject, e.g., a patient. The treatment can be to cure, heal, alleviate, relieve, alter, remedy, ameliorate, palliate, improve or affect the cancer, the symptoms of the cancer or the predisposition toward the cancer.

As used herein, the term "subject" is intended to include human and non-human animals. Non-human animals include all vertebrates, e.g., mammals and non-mammals, such as non-human primates, sheep, dog, cow, chickens, amphibians, reptiles, etc.

As used herein, the term "cancer" includes all types of cancerous growths or oncogenic processes, metastatic tissues or malignantly transformed cells, tissues, or organs, irrespective of histopathologic type or stage of invasiveness.

As used herein, the terms "maximum tolerated dose (MTD)" refers to the dose of any therapeutic drug—including targeted drugs—above which unacceptable toxicity occurs. This is true whether the drugs are targeted to a particular cell type or a particular molecule. Because of the MTD and the limit of tolerability of a drug (targeted or otherwise), maximal anti-cancer efficacy is generally not attainable. The MTD of a drug is impacted significantly by its biodistribution and its pharmacokinetics.

As used herein, the term "biodistribution" refers to the organs and tissues to which a drug distributes in the body.

As used herein, the term "pharmacokinetics" refers to how long a drug stays in the body.

In certain embodiments, the cancer is prostate cancer, neuroendocrine cancer, breast cancer, or non-Hodgkin's lymphoma. In some embodiments, the cancer is a primary tumor, while in other embodiments, the cancer is a secondary or metastatic tumor.

As used herein, the "targeting component" is a component that is able to bind to or otherwise associate with a molecular target, for example, a membrane component, a cell surface receptor, prostate specific membrane antigen (PSMA, which is also known as folate hydrolase 1, glutamate carboxypeptidase II, and NAALADase), or the like. A first and second agent comprising the targeting component may become localized or converge at a particular targeted site, for instance, a tumor, a disease site, a tissue, an organ, a type of cell, etc. As such, the first and second agent may be "target-specific." In some cases, the therapeutic agent may exert its anti-cancer effect without the need for release from the targeting component. In other cases, the therapeutic component may be released from the first and/or second agent and allowed to interact locally with the particular targeting site.

For example, contemplated targeting components may include a nucleic acid, peptide, polypeptide, protein, glycoprotein, carbohydrate, or lipid. A targeting component may be a naturally occurring or synthetic ligand for a cell surface receptor, e.g., a growth factor, hormone, LDL, transferrin, etc. A targeting component can be an antibody, which term is intended to include antibody fragments, characteristic portions of antibodies, single chain targeting moieties which can be identified, for example, using procedures such as phage display. Targeting components may also be a targeting peptide, targeting peptidomimetic, or a small molecule, whether naturally-occurring or artificially created (e.g., via chemical synthesis).

In one embodiment, the first and second targeting components are independently selected from the group consisting of an antibody or binding fragment thereof, a protein, a peptide, oligonucleotide, and a small molecule.

Antibodies against molecular targets on tumors are known. For example, antibodies and antibody fragments which specifically bind markers produced by or associated with tumors have been disclosed, inter alia, in U.S. Pat. No. 3,927,193 to Hansen, and U.S. Pat. Nos. 4,331,647, 4,348,376, 4,361,544, 4,468,457, 4,444,744, 4,818,709 and 4,624,846 to Goldenberg, the contents of all of which are incorporated herein by reference in their entirety. In particular, antibodies against an antigen, e.g., a gastrointestinal, lung, breast, prostate, ovarian, testicular, brain or lymphatic tumor, a sarcoma or a melanoma, are advantageously used. Antibodies to cancer-related antigens are well known to those in the art.

The antibodies of the present invention may exist in a variety of forms including, for example, polyclonal antibodies, monoclonal antibodies, intracellular antibodies ("intrabodies"), antibody fragments (e.g. Fv, Fab and F(ab)2), half-antibodies, hybrid derivatives, as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli,*" *Proc. Natl. Acad. Sci. USA* 85:5879-5883 (1988); Bird et al, "Single-Chain Antigen-Binding Proteins," *Science* 242:423-426 (1988), each of which is hereby incorporated by reference in its entirety).

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the present invention or the synthesis of an amino acid sequence specifying the antibody, where the DNA or amino acid sequence has been obtained using synthetic DNA or amino acid sequence technology which is available and well known in the art.

Methods for monoclonal antibody production may be carried out using the techniques described herein or are well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest either in vivo or in vitro.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. A human antibody is an antibody produced by a human or an antibody having an amino acid sequence corresponding to an antibody produced by a human.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')2 fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

The peptides used in conjunction with the present invention can be obtained by known isolation and purification protocols from natural sources, can be synthesized by standard solid or solution phase peptide synthesis methods according to the known peptide sequence of the peptide, or can be obtained from commercially available preparations. Included herein are peptides that exhibit the biological binding properties of the native peptide and retain the specific binding characteristics of the native peptide. Derivatives and analogs of the peptide, as used herein, include modifications in the composition, identity, and derivitization of the individual amino acids of the peptide provided that the peptide retains the specific binding properties of the native peptide. Examples of such modifications would include modification of any of the amino acids to include the D-stereoisomer, substitution in the aromatic side chain of an aromatic amino acid, derivitization of the amino or carboxyl groups in the side chains of an amino acid containing such a group in a side chain, substitutions in the amino or carboxy terminus of the peptide, linkage of the peptide to a second peptide or biologically active moiety, and cyclization of the peptide (G. Van Binst and D. Tourwe, "Backbone Modifications in Somatostatin Analogues: Relation Between Conformation and Activity," *Peptide Research* 5:8-13 (1992), which is hereby incorporated by reference in its entirety).

In one embodiment, the first and second targeting components target the same molecular target. For example, the first and second targeting components may bind to the same receptor (e.g. PSMA) expressed by the same cell type.

In another embodiment, the first and second targeting components target different molecular targets on the same cell type. For example, the first and second targeting components may bind to different receptors (e.g. HER1 and HER2) expressed on the same cell type.

As used herein, the "cancer therapeutic component" is an agent, or combination of agents, that treats a cell, tissue, or subject having a condition requiring therapy, when contacted with the cell, tissue or subject. The first and second cancer therapeutic components may be the same or different, and may be, for example, therapeutic radionuclides, chemotherapeutic agents, hormones, hormone antagonists, receptor antagonists, enzymes or proenzymes activated by another agent, biologics, autocrines or cytokines. Toxins also can be used in the methods of the present invention. Other therapeutic agents useful in the present invention include anti-DNA, anti-RNA, radiolabeled oligonucleotides, such as anti-sense oligodeoxy ribonucleotides, anti-protein and anti-chromatin cytotoxic or antimicrobial agents. Other therapeutic agents are known to those skilled in the art, and the use of such other therapeutic agents in accordance with the present invention is specifically contemplated.

While the first and second cancer therapeutic components may be the same, in one embodiment they are different. For example, the first and second cancer therapeutic components may comprise different radionuclides, or the first cancer therapeutic component may comprise a chemotherapeutic agent while the second cancer therapeutic component comprises a radionuclide, or the first cancer therapeutic component may comprise a radionuclide while the second cancer therapeutic component comprises a chemotherapeutic agent.

In one embodiment, the first and second cancer therapeutic components are independently selected from the group consisting of a radionuclide and a chemotherapeutic agent.

In one embodiment, the first and/or second cancer therapeutic component is a radionuclide independently selected from the group consisting of $^{86}$Re, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{166}$Dy, $^{166}$Ho, $^{149}$Pm, $^{151}$Pm, $^{153}$Sm, $^{159}$Gd, $^{172}$Tm, $^{169}$Yb, $^{175}$Yb, $^{177}$Lu, $^{105}$Rh, $^{111}$Ag, $^{131}$I, $^{177m}$Sn, $^{225}$Ac, $^{227}$Th, $^{211}$At, and combinations thereof.

Procedures for labeling agents with radioactive isotopes are generally known in the art. For example, there are a wide range of moieties which can serve as chelating ligands and which can be derivatized to the targeting component of the invention. For instance, the chelating ligand can be a derivative of 1,4,7,10-tetraazacyclododecanetetraacetic acid (DOTA), ethylenediaminetetraacetic acid (EDTA), diethylenetriaminepentaacetic acid (DTPA), and 1-p-Isothiocyanato-benzyl-methyl-diethylenetriaminepentaacetic acid (ITC-MX). These chelators typically have groups on the side chain by which the chelator can be used for attachment to a targeting component of the present invention. Such groups include, e.g., benzylisothiocyanate, by which the DOTA, DTPA, or EDTA can be coupled to, e.g., an amine group of the targeting component. Procedures for iodinating biological agents, such as antibodies, binding portions thereof, probes, or ligands, are described by Hunter and Greenwood, "Preparation of Iodine-131 Labelled Human Growth Hormone of High Specific Activity," *Nature* 144:496-496 (1962), David et al., "Protein Iodination With Solid State Lactoperoxidase," *Biochemistry* 13:1014-1021 (1974), and U.S. Pat. No. 3,867,517 to Ling and U.S. Pat. No. 4,376,110 to David, which are hereby incorporated by reference in their entirety. Other procedures for iodinating biological agents are described by Greenwood et al., "The Preparation of I-131-Labelled Human Growth Hormone of High Specific Radioactivity," *Biochem. J.* 89:114-123 (1963); Marchalonis, "An Enzymic Method for the Trace Iodination of Immunoglobulins and Other Proteins," *Biochem. J.* 113: 299-305 (1969); and Morrison et al., "Use of Lactoperoxidase Catalyzed Iodination in Immunochemical Studies," *Immunochemistry* 8:289-297 (1971), which are hereby incorporated by reference in their entirety. Procedures for $^{99m}$Tc-labeling are described by Rhodes, B. et al. in Burchiel, S. et al. (eds.), Tumor Imaging: The Radioimmunochemical Detection of Cancer, New York: Masson 111-123 (1982) and the references cited therein, which are hereby incorporated by reference in their entirety. Procedures suitable for 111 In-labeling biological agents are described by Hnatowich et al., "The Preparation of DTPA-coupled Antibodies Radiolabeled With Metallic Radionuclides: an Improved Method," *J. Immul. Methods* 65:147-157 (1983), Hnatowich et al., "Coupling Antibody With DTPA—an Alternative to the Cyclic Anhydride," *Int. J. Applied Radiation* 35:554-557 (1984), and Buckley et al., "An Efficient Method For Labelling Antibodies With 111In," *F.E.B.S.* 166:202-204 (1984), which are hereby incorporated by reference in their entirety.

In another embodiment, the first and/or second cancer therapeutic component is a chemotherapeutic agent independently selected from the group consisting of busulfan, cisplatin, carboplatin, chlorambucil, cyclophosphamide, ifosfamide, dacarbazine (DTIC), mechlorethamine (nitrogen mustard), melphalan carmustine (BCNU), lomustine (CCNU), 5-fluorouracil (5-FU), capecitabine, methotrexate, gemcitabine, cytarabine (ara-C), fludarabine dactinomycin, daunorubicin, doxorubicin (Adriamycin), idarubicin, mitoxantrone, paclitaxel, docetaxel, etoposide (VP-16), vinblastine, vincristine, vinorelbine prednisone, dexamethasone, tamoxifen, fulvestrant, anastrozole, letrozole, megestrol acetate, bicalutamide, flutamide, leuprolide, goserelin, L-asparaginase, tretinoin, maytansines, auristatins, pyrrolobenzodiazepines, duocarmycins, and combinations thereof.

Procedures for conjugating biological agents with chemotherapeutic agents are well known in the art. Most of the chemotherapeutic agents currently in use in treating cancer possess functional groups that are amenable to chemical crosslinking directly with an amine or carboxyl group of a targeting component of the present invention. For example, free amino groups are available on methotrexate, doxorubicin, daunorubicin, cytosinarabinoside, cisplatin, vindesine, mitomycin, and bleomycin while free carboxylic acid groups are available on methotrexate, melphalan, and chlorambucil. These functional groups, that is free amino and carboxylic acids, are targets for a variety of homo-bifunctional and hetero-bifunctional chemical crosslinking agents which can crosslink these drugs directly to a free amino group of a targeting component. Specific procedures for conjugating targeting components with chemotherapeutic agents have been described and are known in the art. By way of example, conjugation of chlorambucil with antibodies is described by Flechner, "The Cure and Concomitant Immunization of Mice Bearing Ehrlich Ascites Tumors by Treatment With an Antibody—Alkylating Agent Complex," *European Journal of Cancer* 9:741-745 (1973); Ghose et al., "Immunochemotherapy of Cancer with Chlorambucil-Carrying Antibody," *British Medical Journal* 3:495-499 (1972); and Szekerke et al., "The Use of Macromolecules as Carriers of Cytotoxic Groups (part II) Nitrogen Mustard—Protein Complexes," *Neoplasma* 19:211-215 (1972), which are hereby incorporated by reference in their entirety. Procedures for conjugating daunomycin and adriamycin to antibodies are described by Hurwitz et al., "The Covalent Binding of Daunomycin and Adriamycin to Antibodies, With Retention of Both Drug and Antibody Activities," *Cancer Research* 35:1175-1181 (1975) and Arnon et al. *Cancer Surveys* 1:429-449 (1982), which are hereby incorporated by reference in their entirety. Coupling procedures as also described in EP 86309516.2, which is hereby incorporated by reference in its entirety.

It will be appreciated that the exact dosage of the first and second agents of the invention is chosen by the individual physician in view of the patient to be treated. In general, dosage and administration are adjusted to provide an effective amount of the agent to the patient being treated. As used herein, the "effective amount" of an agent refers to the amount necessary to elicit the desired biological response. As will be appreciated by those of ordinary skill in this art, the effective amount of agent of the invention may vary depending on such factors as the desired biological endpoint, the drug to be delivered, the target tissue, the route of administration, etc. For example, the effective amount of agent containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

In general, doses can range from about 25% to about 100% of the MTD of the targeted agent when given as a single agent. Based upon the composition, the dose can be delivered once, continuously, such as by continuous pump, or at periodic intervals. Dosage may be adjusted appropriately to achieve desired drug levels, locally, or systemically. In the event that the response in a subject is insufficient at such doses, even higher doses (or effective higher doses by a different, more localized delivery route) may be employed to the extent that patient tolerance permits. Continuous IV dosing over, for example, 24 hours or multiple doses per day also are contemplated to achieve appropriate systemic levels of compounds.

In one embodiment, the first and second cancer therapeutic components each have a maximum tolerated dose, and the maximum tolerated doses of the first and second cancer therapeutic components are administered to the subject. Because the biodistribution and pharmacokinetics are different for the two targeting components, their toxicities as individual drugs are non- or minimally overlapping. As a result, the increased, additive dose to the target site is not accompanied by a commensurate increase in toxicity.

In an alternative embodiment, less than the maximum tolerated doses of the first and second cancer therapeutic components are administered to the subject. When the two therapeutic components are combined in a treatment strategy in amounts less than the maximum tolerated dose, the result is that both drugs converge (simultaneously or sequentially) at the desired target site thereby providing an additive treatment effect but, because the agents are administered at less than their MTD, lower toxicity is experienced by the subject.

In one embodiment, the first agent is an antibody conjugated to a radionuclide and is administered at a dose of about 100 to 160 mCi total in a 2 week cycle, such as a dose of 100, 110, 120, 130, 140, 150, or 160 mCi total in a 2 week cycle.

In another embodiment, the first agent is an antibody conjugated to a radionuclide and is administered at a dose of about 120 to 140 mCi total in a 2 week cycle, such as a dose of 120, 125, 130, or 140 mCi total in a 2 week cycle.

In a further embodiment, the second agent is a small molecule conjugated to a radionuclide and is administered at a dose of about 300 to 500 mCi total in a 2 week cycle, such as a dose of 300, 325, 350, 375, 400, 425, 450, 475, or 500 mCi total in a 2 week cycle.

In practicing the methods of the present invention, the administering step is carried out to treat cancer in a subject.

In one embodiment, a subject having cancer is selected prior to the administering step. Such administration can be carried out systemically or via direct or local administration to the tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent (e.g., an antibody or an inhibitory nucleic acid molecule) and the disease to be treated.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the agents of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt According to one embodiment of the present invention, the cancer is prostate cancer.

In another embodiment of this aspect of the invention, when the cancer is prostate cancer, the first and second targeting components target the PSMA receptor.

As used herein, "PSMA" or "prostate-specific membrane antigen" protein refers to mammalian PSMA, preferably human PSMA protein. The long transcript of PSMA encodes a protein product of about 100-120 kDa molecular weight characterized as a type II transmembrane receptor having sequence homology with the transferrin receptor and having NAALADase activity (Carter et al., "Prostate-Specific Membrane Antigen is a Hydrolase With Substrate and Pharmacologic Characteristics of a Neuropeptidase," *Proc. Natl. Acad. Sci. USA* 93:749-753 (1996), which is hereby incorporated by reference in its entirety).

In an alternative embodiment, the first targeting component is a PSMA receptor antibody and the second targeting component is a PSMA receptor binding peptide or PSMA receptor inhibitor.

A PSMA receptor antibody is an antibody that interacts with (e.g., binds to) PSMA, preferably human PSMA protein. Preferably, the PSMA receptor antibody interacts with, e.g., binds to, the extracellular domain of PSMA, e.g., the extracellular domain of human PSMA located at about amino acids 44-750 of human PSMA (amino acid residues correspond to the human PSMA sequence disclosed in U.S. Pat. No. 5,538,866, which is hereby incorporated by reference in its entirety). PSMA receptor antibodies are known in the art (Goldsmith et al., "Targeted Radionuclide Therapy for Prostate Cancer," in *Therapeutic Nuclear Medicine* 617-628 (R. Baum ed. 2014), which is hereby incorporated by reference in its entirety). Exemplary PSMA receptor antibodies include, but are not limited to, J591, J415, J533, and E99.

The PSMA receptor inhibitor may include any lipids, carbohydrates, polynucleotides, peptides, polypeptides, or any other biologic, organic or inorganic molecules which inhibit the function of the PSMA receptor. Exemplary PSMA receptor inhibitor are known in the art include, but are not limited to, PSMA 617, PSMA I&T, DCFBC, DCFPyL, glutamate-urea-lysine analogs, phosphoramidate analogs, and 2-(phosphinylmethyl) pentanedioic acid analogs (Lutje et al., "PSMA Ligands for Radionuclide Imaging and Therapy of Prostate Cancer: Clinical Status," *Theranostics* 5(12):1388-1401 (2015); Haberkorn et al., "New Strategies in Prostate Cancer: Prostate-Specific Membrane Antigen (PSMA) Ligands for Diagnosis and Therapy," *Clin. Cancer Res.* 22(1):9-15 (2016), which are hereby incorporated by reference in their entirety).

In one embodiment, the PSMA receptor antibody is selected from the group consisting of J591, J415, J533, and E99, while the second targeting component is a peptide selected from the group consisting of PSMA 617, PSMA I&T, DCFBC, DCFPyL, glutamate-urea-lysine analogs, phosphoramidate analogs, 2-(phosphinylmethyl) pentanedioic acid analogs, and other PSMA ligands/inhibitors.

In one embodiment, the first agent is J591-$^{177}$Lu and the second agent is PSMA 617-$^{177}$Lu or PSMA I&T-$^{177}$Lu. By way of example, the PSMA receptor antibodies can be radiolabeled with $^{111}$Indium, $^{90}$Yttrium, or $^{177}$Lutetium by coupling with 1,4,7,10-tetraazacyclododecane-N,N',N'',N'''-tetraacetic acid (DOTA) as described in U.S. Pat. No. 7,045,605 to Bander, which is hereby incorporated by reference in its entirety.

In another embodiment of the present invention, the cancer is a neuroendocrine cancer. Neuroendocrine cancers include, but are not limited to, carcinoid tumors, gastrinoma, insulinoma, glucagonoma, VIPoma, somatostatinoma, thyroid carcinoma, Merkel cell carcinoma of the skin, tumor of the anterior pituitary, medullary carcinoma, parathyroid tumor, thymus and mediastinal carcinoid tumor, pulmonary neuroendocrine tumor, adrenomedullary tumor, pheochromocytoma, Schwannoma, paraganglioma, neuroblastoma, and urinary tract carcinoid neuroendocrine carcinoma.

In accordance with this aspect of the present invention, in one embodiment, the first and second targeting components target the somatostatin receptor.

At least five somatostatin receptors subtypes have been characterized and tumors can express various receptor subtypes (Shaer et al., "Somatostatin Receptor Subtypes sst1, sst2, sst3 and sst5 Expression in Human Pituitary, Gastroentero-Pancreatic and Mammary tumors: Comparison of mRNA Analysis With Receptor Autoradiography," *Int. J. Cancer* 70:530-537 (1997), which is hereby incorporated by reference in its entirety). Naturally occurring somatostatin and its analogs exhibit differential binding to these receptor subtypes, allowing precise targeting of a peptide analog to specific diseased tissues.

In accordance with this aspect of the invention, the first and second targeting components have at least one biological activity of native somatostatin; preferably, this activity is the ability to specifically bind to a somatostatin receptor on a somatostatin receptor-bearing cell. Many such analogs having biological activity are known and have been described, for example, in U.S. Pat. No. 5,770,687 to Hornik et al.; U.S. Pat. No. 5,708,135 to Coy et al.; U.S. Pat. No. 5,750,499 to Hoeger et al; U.S. Pat. No. 5,620,675 to McBride et al.; U.S. Pat. No. 5,633,263 to Coy et al; U.S. Pat. No. 5,597,894 to Coy et al; U.S. Pat. No. 5,073,541 to Taylor et al; U.S. Pat. No. 4,904,642 to Coy et al; U.S. Pat. No. 6,017,509 to Dean; WO 98/47524 to Hoffman et al.; and U.S. Pat. No. 5,411,943 to Bogden, each of which is hereby incorporated by reference in its entirety.

In one embodiment, the first and second targeting components target the somatostatin receptor-2.

In another embodiment of the present invention the cancer is breast cancer.

In accordance with this embodiment of the present invention, when the cancer is breast cancer, the first and second targeting components target the HER receptor family.

First and second agents, as well as targeting and therapeutic components, are described above.

In another embodiment of the present invention the cancer is non-Hodgkin's Lymphoma.

In accordance with this embodiment, when the cancer is non-Hodgkin's lymphoma, the first and second targeting components target CD20.

First and second agents, as well as targeting and therapeutic components, are described above.

Another aspect of the present invention relates to a combination therapeutic for treating cancer. The combination therapeutic includes a first agent comprising a first targeting component coupled to a first cancer therapeutic component and a second agent comprising a second targeting component coupled to a second cancer therapeutic component. The first and second targeting components have different biodistributions and/or pharmacokinetics.

First and second agents, as well as targeting and therapeutic components, are described above.

Pharmaceutical compositions containing agents for use in the methods of the present invention can include a pharmaceutically acceptable carrier as described infra, one or more active agents, and a suitable delivery vehicle. Suitable delivery vehicles include, but are not limited to, viruses, bacteria, biodegradable microspheres, microparticles, nanoparticles, liposomes, collagen minipellets, and cochleates.

In one embodiment of the present invention, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010), WO2011/034798 to Bumcrot et al., WO2009/111658 to Bumcrot et al., and WO2010/105209 to Bumcrot et al., which are hereby incorporated by reference in their entirety.

In another embodiment of the present invention, the delivery vehicle is a nanoparticle. A variety of nanoparticle delivery vehicles are known in the art and are suitable for delivery of an inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly (ethylene glycol) Copolymers As Novel Gene Carriers," *J Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment of the present invention, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size, and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda, and U.S. Pat. No. 5,059,421 to Loughrey et al., which are hereby incorporated by reference in their entirety.

In another embodiment of the present invention, the delivery vehicle is a viral vector. Viral vectors are particularly suitable for the delivery of inhibitory nucleic acid molecules, such as siRNA or shRNA molecules, but can also be used to deliver molecules encoding an anti-integrin antibody. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988), Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Regardless of the type of infective transformation system employed, it should be targeted for delivery of the nucleic acid to the desired cell type. For example, for delivery into a cluster of cells (e.g., cancer cells) a high titer of the infective transformation system can be injected directly within the site of those cells so as to enhance the likelihood of cell infection. The infected cells will then express the inhibitory nucleic acid molecule targeting the inhibition of integrin expression. The expression system can further contain a promoter to control or regulate the strength and specificity of expression of the nucleic acid molecule in the target tissue or cell.

Effective doses of the compositions of the present invention, for the treatment of a metastatic disease vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

EXAMPLES

The examples below are intended to exemplify the practice of embodiments of the disclosure but are by no means intended to limit the scope thereof.

Materials and Methods

Internalization assay. LNCaP and CWR22Rv1 cells were trypsinized and aliquoted into tubes at $1 \times 10^6$ cells per tube. Cells were washed once with RPMI (no FBS). $^{177}$Lu-J591 (150,000 CPM) in 2004 RPMI (no FBS) per tube and/or $^{177}$Lu-PSMA-617 (110,000 CPM) was added in 2004 RPMI (no FBS) per tube. The samples were incubated for 1 hour at 37° C., with the cells re-suspended every 15 minutes. After incubation, the cells were washed twice with 0.1% BSA/PBS to remove unbound/un-internalized binding agents. Samples were counted.

LNCaP xenografts. Each BALB/c$^{nu/nu}$ male mouse was implanted subcutaneously with 5 million LNCaP cells (with Matrigel). Ten days later, mice were randomly sorted into groups of 5 with similar tumor volume. On day 0, 177 Lu-J591, 177 Lu-PSMA617, or PBS was injected via tail vein at various doses. Tumor volume and mouse weight were measured 2-3 times per week. Tumor volume was calculated using the formula 0.52*L*L*W and plotted against time (days post-treatment).

CWR22Rv1 xenografts. Each BALB/c$^{nu/nu}$ male mouse was implanted subcutaneously with 5 million CWR22Rv1 cells (with Matrigel). Four days later, mice were sorted into groups of 5 to achieve similar tumor volume. $^{177}$Lu-J591, 177 Lu-PSMA617, or PBS was injected via tail vein at the indicated doses. Tumor volume and mouse weight were measured 2-3 times per week. Tumor volume was calculated using the formula 0.52*L*L*W and plotted against time (days post-treatment).

Figure 1B:
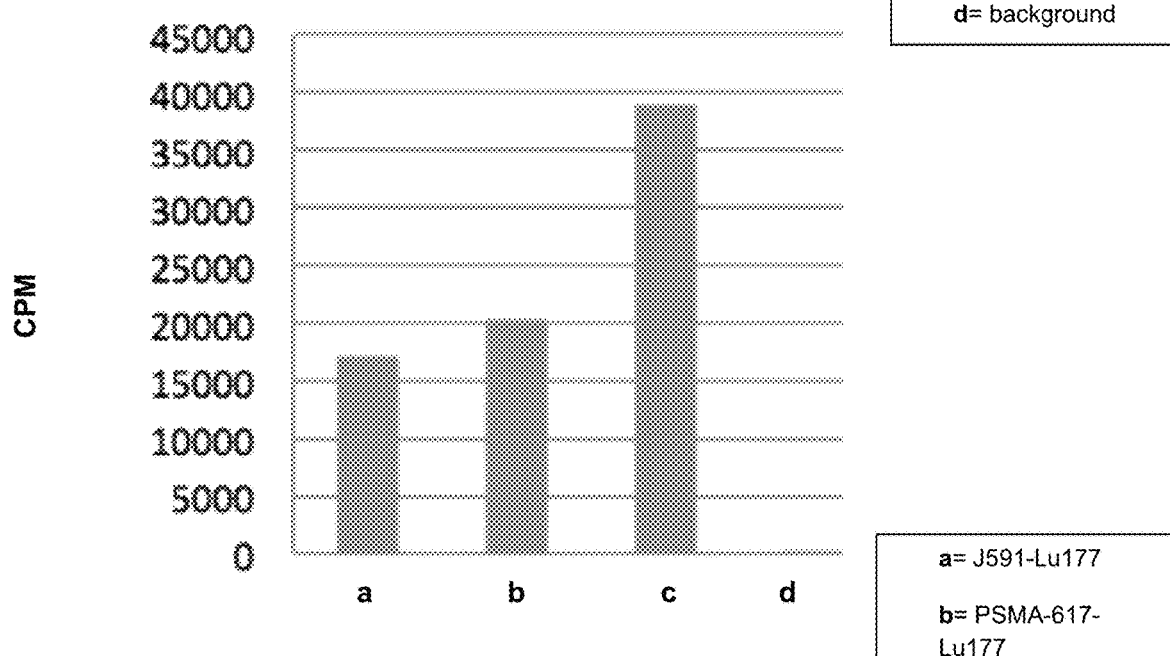

Example 1—Co-Incubation of Radiolabeled Anti-PSMA Antibody J591-$^{177}$Lu and Radiolabeled PSMA-617-$^{177}$Lu Results in Additive $^{177}$Lu Internalization in PSMA-Positive Cells In Vitro The individual agents, J591-$^{177}$Lu and PSMA-617-$^{177}$Lu, each internalized to a similar degree within either given cell line (LNCaP and CWR22Rv1) (FIGS. 1A-1B). Internalization was greater in LNCaP than CWR22Rv1, consistent with the higher PSMA expression in the LNCaP cell line. When both agents were co-incubated, both co-internalized effectively leading to an additive amount of radiolabel within the cells.

Figure 2:
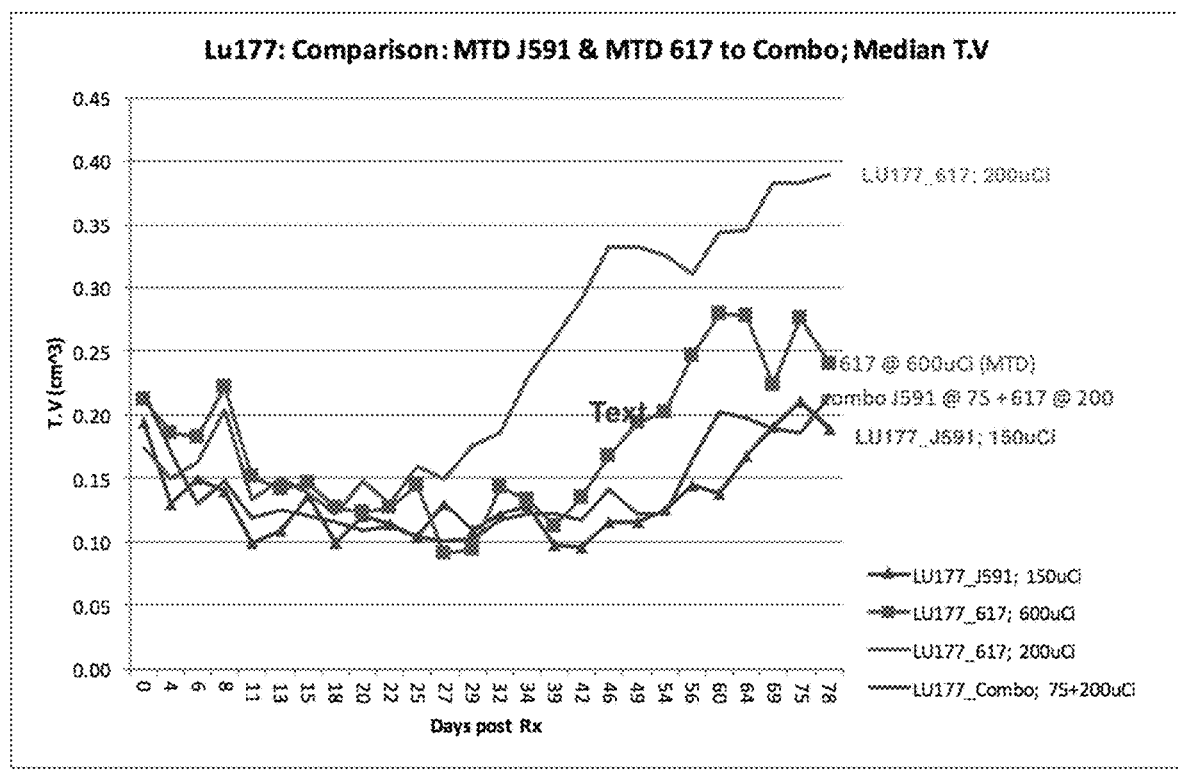
FIG. 2 shows that an anti-tumor effect could be achieved in LNCaP xenografts at half the dose of J591-$^{177}$Lu (i.e., 75 µCi) by also adding a dose of PSMA-617-$^{177}$Lu (i.e., 200 µCi) well below its MTD.

Example 2—Combined Treatment Using Radiolabeled Anti-PSMA Antibody J591-$^{177}$Lu and Radiolabeled PSMA-617-$^{177}$Lu Results in Additive Anti-Tumor Effect In Vivo In the LNCaP xenografts, PBS-treated animals (placebo control) developed tumors of approximately 1 cm in diameter by day 25 and required sacrifice several days later. The best anti-tumor effect was achieved by J591-$^{177}$Lu at 150 µCi (FIG. 2). Equal anti-tumor effect could be achieved at half the dose of J591-$^{177}$Lu (i.e., 75 µCO by also adding a dose of PSMA-617-$^{177}$Lu (i.e., 200 µCi) well below its MTD (FIG. 2).

Figure 3:
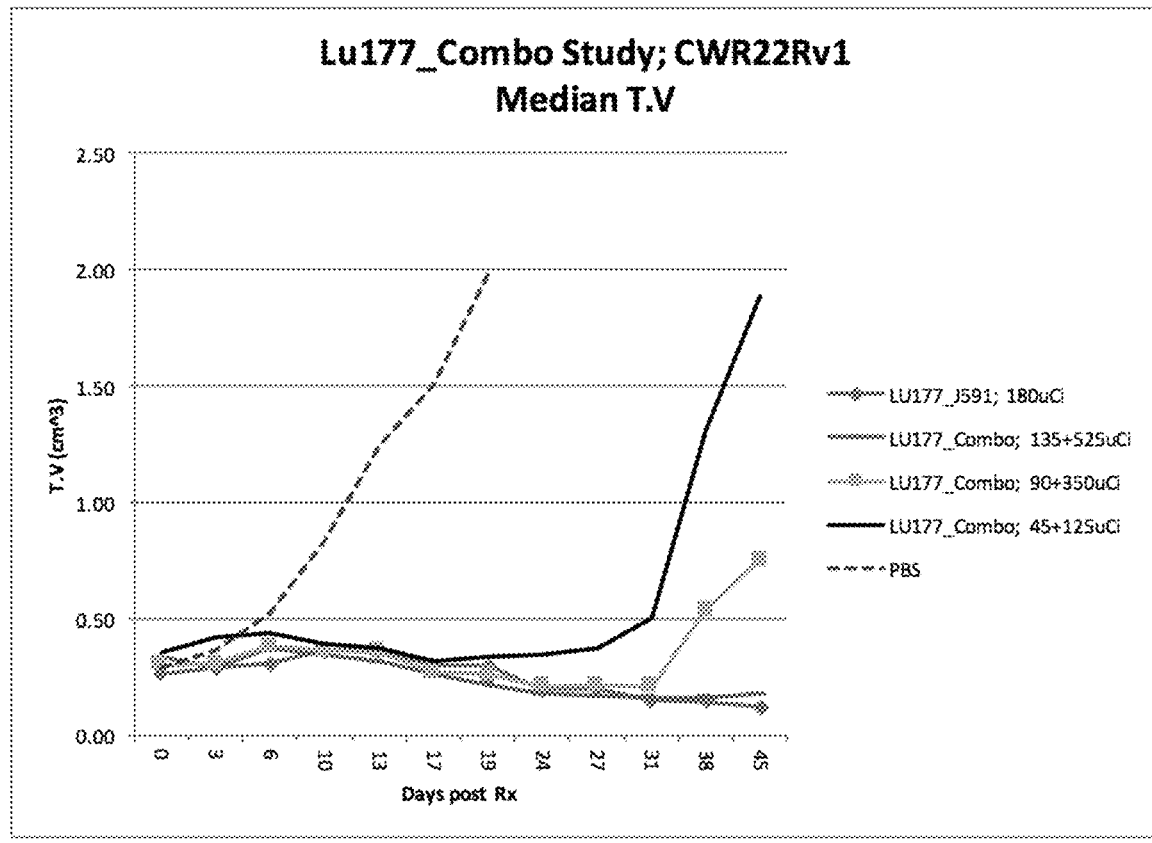
FIG. 3 shows the anti-tumor response of J591-$^{177}$Lu at its MTD could be equaled by J591-$^{177}$Lu at 135 µCi (75% of MTD) plus 525 µCi (a sub-MTD dose) of PSMA-617-$^{177}$Lu.
Figure 4:
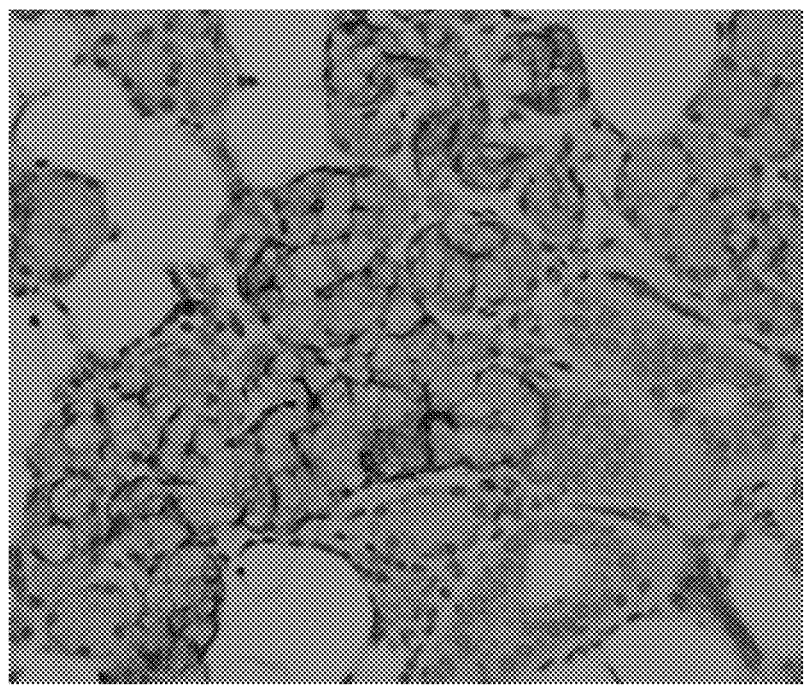
FIG. 4 shows expression of PSMA in human salivary gland alveoli.
Figure 5A:
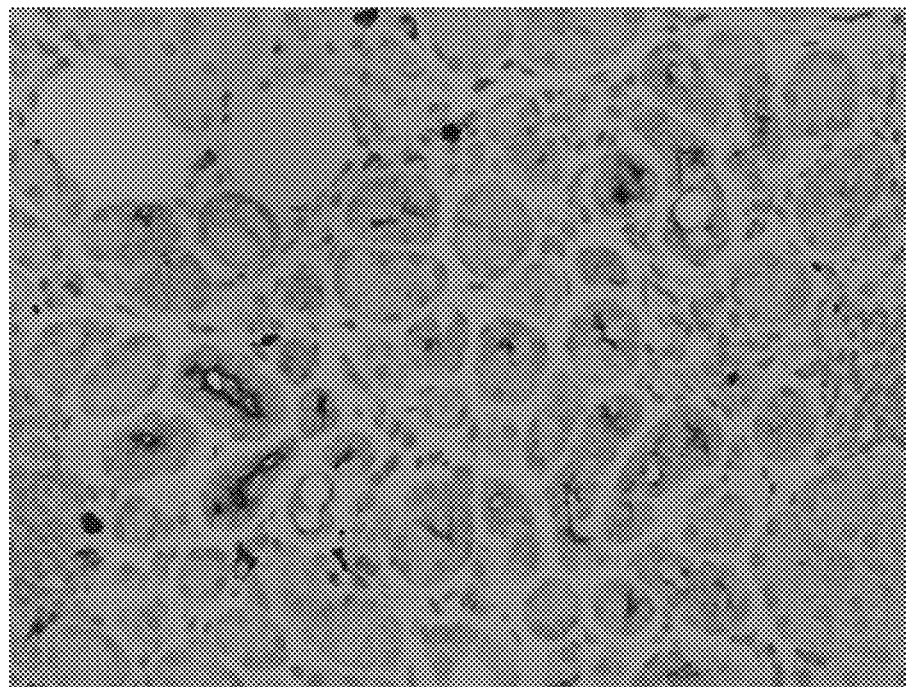
FIGS. 5A-5B show expression of PSMA in human salivary gland intercalated ducts at 20× magnification (FIG. 5A) and at 10× magnification (FIG. 5B).
Figure 5B:
Figure 6A:
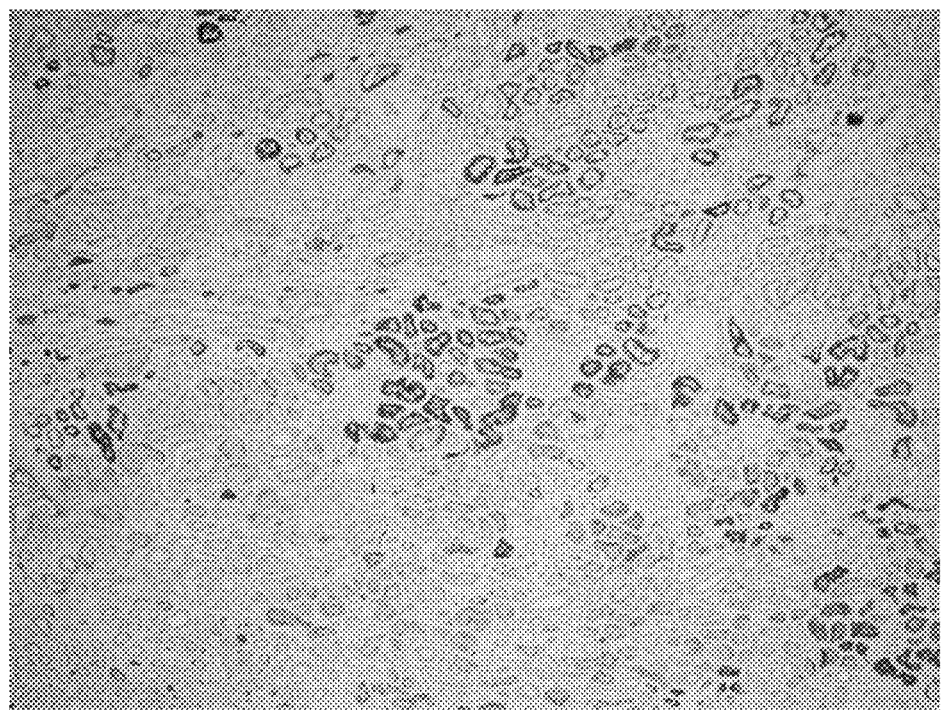
FIGS. 6A-6B show expression of PSMA in human kidney at 4× magnification (FIG. 6A) and at 10× magnification (FIG. 6B).
Figure 6B:
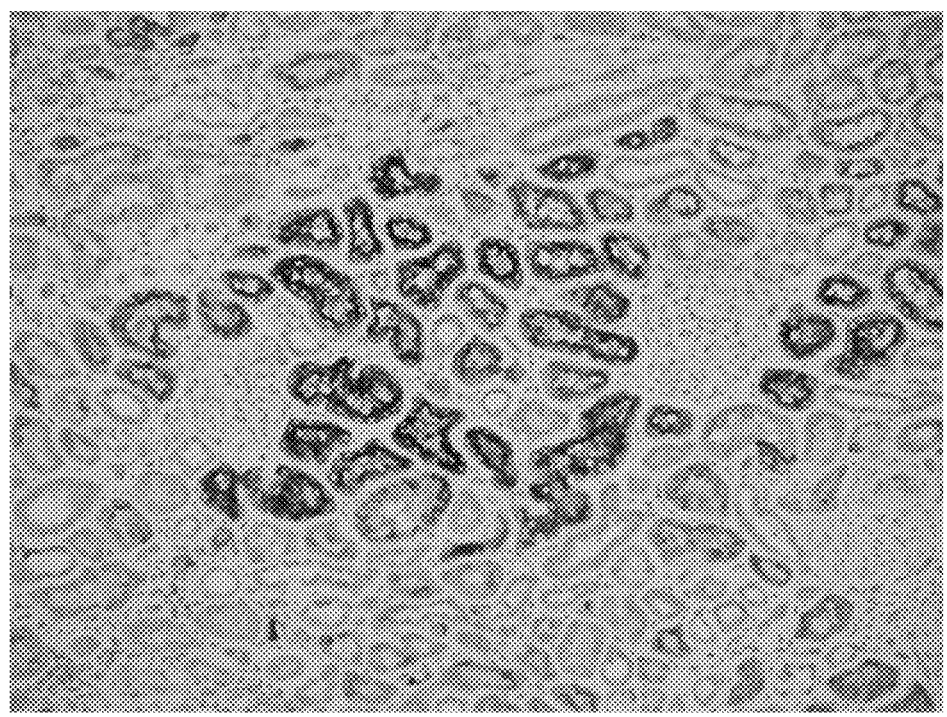
Figure 7:
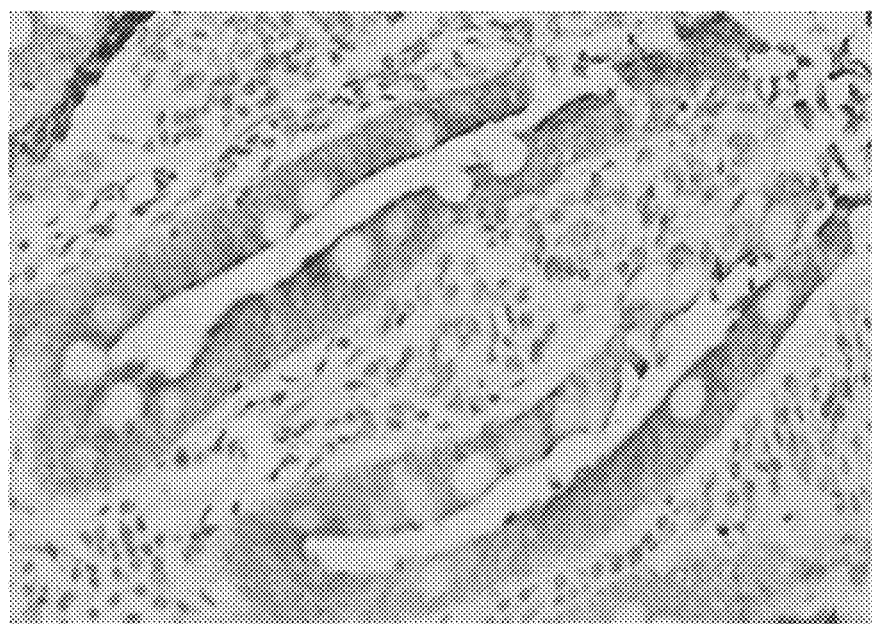
FIG. 7 shows expression of PSMA in small bowel.

In the CWR22Rv1 xenografts, placebo (PBS)-treated mice required sacrifice by day 17. J591-$^{177}$Lu, at the MTD dose of 180 µCi, demonstrated the best anti-tumor response (FIG. 3). This response could be equaled by J591-$^{177}$Lu at 135 µCi (75% of MTD) plus 525 µCi (a sub-MTD dose) of PSMA-617-$^{177}$Lu (FIG. 3).

Discussion of Examples 1-2

Taken together, these data show that co-administering 2 agents that bind different sites of a target molecule (e.g., a cell surface receptor molecule) present on a population of cells results in additive binding of those agents. Where the target molecule/receptor is internalized, additive amounts of the 2 agents will, therefore, be internalized. Furthermore, if the 2 targeting agents have different properties (e.g., molecular mass, charge, hydrophilicity/hydrophobicity, pharmacokinetics, bio-distribution, etc.) such that their respective side effects differ, and are non-overlapping, the 2 agents can be co-administered to result in additive binding/uptake by the targeted cells without causing any added toxicity. As a corollary, the dose of each agent can be modestly reduced (by 5-50%) below its respective maximum tolerated dose whereby the co-administration of the 2 targeting agents still provides an additive dose to the target cells but can substantially or completely reduce the toxicity experienced by the subject.

Prophetic Example 1—Dosing in Human Patients

Tumor-related molecular targets, exemplified by prostate-specific membrane antigen (PSMA), may be targeted in vitro and in vivo either by antibodies or small molecular ligands. These 2 classes of agents differ greatly both in molecular size and plasma half-life.

|  | Antibody | Ligand |
|---|---|---|
| Size (molecular weight) | 150,000 | 1,400* |
| Plasma half-life | 3-7 days | 3-7 hours |

*includes linker and chelate

As a result of the difference in size and its impact on vascular permeability and ability to penetrate normal tissues, the bio-distribution of these two different classes or types of tumor targeting agents differs. The small molecular weight ligands rapidly extravasate out of the blood vessels, into the extravascular fluid space and into the tissues with little to no barrier to entry. Conversely, large molecular weight molecules such as antibodies (Abs) circulate in the vascular compartment for days to weeks. These far larger agents can traverse reticuloendothelial organs such as the bone marrow and lymph nodes easily but other normal tissue barriers are traversed only slowly particularly in those normal tissues where there are basement membranes, intervening cell layers and epithelial tight junctions. In the case of invasive tumors, these normal barriers are breached by the tumor cells themselves making the tumor cells readily accessible to Abs.

Size also plays a role in how long a molecule stays in the body before it is excreted. For instance, small molecules very easily pass through the kidney glomerulus and are promptly excreted in the urine. This is the case with the small molecule ligands such as those that target PSMA and somatostatin type 2 receptors (SSTR-2). Abs, however, are far too large to pass through the glomerulus so they are not excreted by the urinary tract, stay much longer in the body and are more often metabolized by the liver.

Figure 8A:
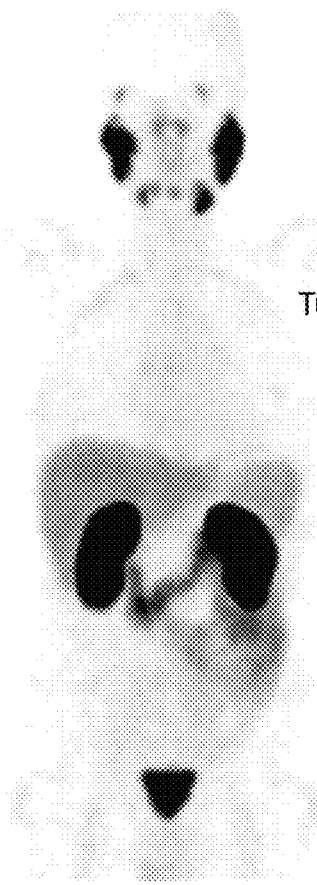
FIGS. 8A-8B show the bio-distribution of PSMA peptides/inhibitors by positron emission tomography with 68 Ga-PSMA 11 (FIG. 8A) (Afshar-Oromieh et al., "PET Imaging With a [68Ga]Gallium-Labelled PSMA Ligand for the Diagnosis of Prostate Cancer: Biodistribution in Humans and First Evaluation of Tumour Lesions," *Eur. J. Nucl. Med. Mol. Imaging* 40(4):486-95 (2013), which is hereby incorporated by reference in its entirety) and 68 Ga-PSMA I&T (FIG. 8B) (Herrmann et. al., "Biodistribution and Radiation Dosimetry for a Probe Targeting Prostate-Specific Membrane Antigen for Imaging and Therapy," *J. Nucl. Med.* 56(6):855-61 (2015), which is hereby incorporated by reference in its entirety).
Figure 8B:
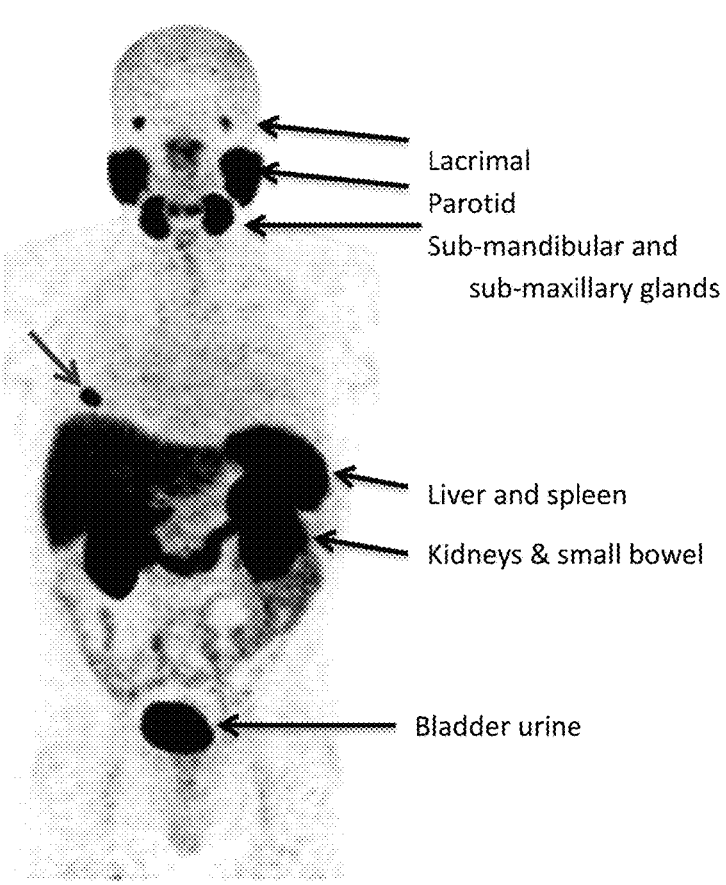
Figures 9A, 9B:
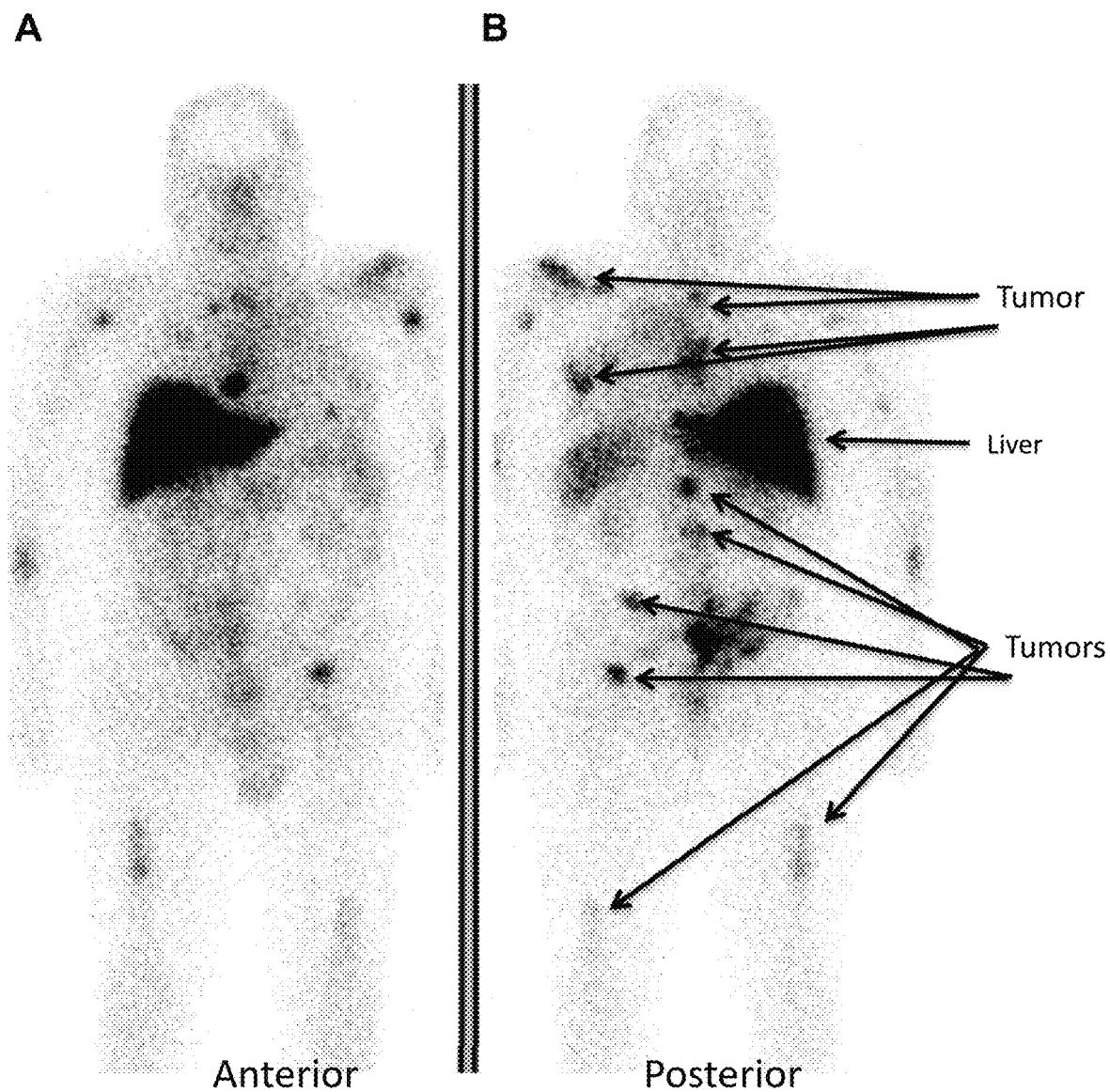
FIGS. 9A-9B show the bio-distribution of Anti-PSMA antibodies by anterior (FIG. 9A) and posterior (FIG. 9B) positron emission tomography.

While the two different classes of agents both bind to their target (e.g., PSMA, SSTR-2, CD20, etc)-expressing tumor cells, the normal tissues that get targeted differs between classes of agents. As an example, PSMA is expressed not only by prostate cancer cells but also by the normal parotid and other salivary glands, lacrimal glands, kidney and small bowel (See FIGS. 4-7). Small molecule/inhibitor-based PSMA agents target these normal tissue sites—parotid and other salivary glands, lacrimal glands, kidneys and small bowel; anti-PSMA Abs do not target the salivary or other glands nor the kidneys as the Abs are too large to penetrate into these normal tissues. The different bio-distributions of these 2 types of agents, large Abs and small ligands, is demonstrated by imaging scans of patients who were administered each type of agent (FIG. 8 and FIG. 9). With both types of agents, the tumor sites are targeted, but the normal tissues that are targeted are different and virtually mutually exclusive.

By targeting tumors with both of the 2 different types of agents, the tumor gets additive dosing while the non-target normal tissues do not receive additive doses. Another advantage of targeting with 2 different types of agents is that one has the option to use more than 1 type of cytotoxin. For example, with radioisotope therapeutics, one can target an alpha and a beta or 2 alphas or 2 beta particles.

Prophetic Example 2—Beta+Beta

In the case of targeting a beta (e.g., $^{177}$Lu) on an Ab, e.g., J591-Lu$^{177}$ to target PSMA, the key (and dose-limiting) side effect is thrombocytopenia (decreased platelet count), and the relative degree of thrombocytopenia progressively increases in magnitude as the dose increases. While none of the patients treated with J591-Lu$^{177}$ suffered any bleeding episodes, some did require platelet transfusions until their platelet counts naturally recovered. No patients at doses of 30 mCi/m$^2$×2 doses (approx. 120 mCi total in a man of approx. 2.0 m 2) or 35 mCi/m$^2$×2 doses (approx. 140 mCi total) required platelet transfusions, whereas 5 of 16 (31%), and 9 of (60%) patients at 40 mCi/m$^2$×2 doses (approx. 160 mCi total) and 45 mCi/m$^2$×2 doses (approx. 180 mCi total) doses, respectively, did require platelet transfusions to support them while their bone marrow recovered.

| Total dose/activity of J591-Lu administered | # of patients platelet transfusions(%) |
|---|---|
| 120 | 0 |
| 140 | 0 |
| 160 | 5/16 (31%) |
| 180 | 9/16 (60%) |

J591-Lu$^{177}$ begins to induce PSA declines, as an indication of anti-tumor activity, at an administered $^{177}$Lu dose of ≤30 mCi/m$^2$ given twice at a 2 week interval. As the dose is increased to 140, 160 and 180 mCi [total], the magnitude of the PSA/anti-tumor response gets progressively greater.

Kabasakal et. al., "Pre-Therapeutic Dosimetry of Normal Organs and Tissues of $^{177}$Lu-PSMA-617 Prostate-Specific Membrane Antigen (PSMA) Inhibitor in Patients With Castration-Resistant Prostate Cancer," Eur. J. Nucl. Med. Mol. Imaging 42:1976-1983 (2015), which is hereby incorporated by reference in its entirety, and Kratochwil et. al., "PSMA-Targeted Radionuclide Therapy of Metastatic Castration-Resistant Prostate Cancer With $^{177}$Lu-Labeled PSMA-617," J. Nucl. Med. 57:1170-1176 (2016), which is hereby incorporated by reference in its entirety, have determined that the maximum safe cumulative dose of PSMA-617-Lu$^{177}$ (a ligand representative of PSMA-binding small molecule ligands/inhibitors/peptides) is 27-30 Gbq as the limit to the kidney and salivary glands. Doses at this level or beyond subject the patients to potential kidney function compromise and xerostomia (dry mouth). Severe xerostomia results in loss of taste and appetite and severe dental/oral cavity disease. Patients complain about difficulty chewing, swallowing, sleeping, speaking, abnormal taste and a burning sensation in the mouth.

PSMA-617/ligand-Lu$^{177}$ begins to induce PSA declines at an administered cumulative $^{177}$Lu dose of 300 mCi (11.1 Gbq) given in a 2-dose regimen at a 2 week interval (150 mCi×2). As the dose is increased to 2-dose totals of 400-500 mCi (14.8-18.5 GBq), the magnitude of the PSA/anti-tumor response gets progressively greater.

J591-$^{177}$Lu does not deliver large radioactive doses to the kidneys or to the salivary glands, and PSMA-617/ligand does not deliver large doses to the bone marrow so it does not cause thrombocytopenia—that is, these two different targeting agents both lead to anti-tumor activity but their respective side effects are mutually exclusive.

The proposed therapeutic approach seeks to attain maximal dose to the tumor and resulting anti-tumor effect by targeting $^{177}$Lu (or other cytotoxic agents known to those in the art) using a combination of the 2 respective agents: anti-PSMA Ab (e.g., J591) and PSMA ligand/inhibitor/peptide (e.g., PSMA-617, PSMA-11, PSMA I & T, RM-2, etc). By modestly lowering the dose of each agent, the side effects to platelets [due to anti-PSMA Ab] and to kidneys and salivary glands [due to PSMA ligand/inhibitor/peptide] can be reduced or avoided. More specifically, a dose of J591-$^{177}$Lu 120-140 mCi total in a 2 week cycle is proposed. Another possible dose range of J591-$^{177}$Lu is from 100-160 mCi total in a 2 week cycle. The J591-$^{177}$Lu dosing is to be accompanied by contemporaneous dosing of PSMA ligand/inhibitor/peptide (e.g., PSMA-617) of 400 mCi total in a 2 week cycle (or a range of 300-500 mCi total in a 2 week cycle). At these doses, no significant salivary gland or kidney function compromise occurs, and the doses are below the 27-30 Gbq cumulative doses determined by Kabasakal et. al., "Pre-Therapeutic Dosimetry of Normal Organs and Tissues of $^{177}$Lu-PSMA-617 Prostate-Specific Membrane Antigen (PSMA) Inhibitor in Patients With Castration-Resistant Prostate Cancer," *Eur. J. Nucl. Med. Mol. Imaging* 42:1976-1983 (2015), which is hereby incorporated by reference in its entirety, and Kratochwil et. al., "PSMA-Targeted Radionuclide Therapy of Metastatic Castration-Resistant Prostate Cancer With $^{177}$Lu-Labeled PSMA-617," *J. Nucl. Med.* 57:1170-1176 (2016), which is hereby incorporated by reference in its entirety. If desired, 1-2 additional doses of 200-250 mCi (7.4-9.25 Gbq) could be given at ≥2 week interval/s and still remain below the 27-30 Gbq limit.

Prophetic Example 3—Alpha+Alpha

Alpha particles offer significantly more cell killing potential than betas due to their substantially greater atomic mass, linear energy transfer and radiobiological effect. The potential of substantial anti-tumor effect when treating prostate cancer patients with PSMA-617-Ac$^{225}$ has been reported. Unfortunately, this treatment is limited by the intolerable damage done to the salivary glands. Treatment activities of 50 kBq/kg were without toxicity but induced insufficient anti-tumor response in patients with high tumor burden. However, an increase in administered activity led to severe xerostomia becoming the dose-limiting toxicity if treatment activity exceeded 100 kBq/kg per cycle (Kratochwil et. al., "Targeted Alpha-Therapy of Metastatic Castration-Resistant Prostate Cancer With (225)Ac-PSMA-617: Dosimetry Estimate and Empiric Dose Finding," *J. Nucl. Med.* 58(10): 1624-1631 (2017), which is hereby incorporated by reference in its entirety). Although greater anti-tumor activity occurred at higher doses, the side effects were too great. However, this can be improved by delivering additional Ac$^{225}$ to the tumor via the Ab which does not target the salivary glands. The appropriate dose of J591-Ac$^{225}$ can be determined in a standard phase 1 trial in which all patients receive PSMA 617-Ac$^{225}$ at the tolerable dose of 100 Kbq/kg plus escalating doses of J591-Ac$^{225}$ until an MTD is determined. This will result in determination of the dosing of the combination of PSMA ligand-Ac$^{225}$+anti-PSMA Ab-Ac$^{225}$.

Prophetic Example 4—Alpha+Beta

Combining treatment with an alpha particle and its high energy and high cytotoxicity as well as its focused short range along with a beta, which has a longer range, also offers patient benefit as the latter will provide anti-tumor activity at the tumor margins. It is preferred to target the alpha using the Ab so as to avoid the intolerable salivary gland side effects and target the beta using the PSMA ligand to avoid serious hematological toxicity. All patients would receive PSMA 617-Lu$^{177}$ at 400 mCi total in a 2 week cycle (or a range of 300-500 mCi total in a 2 week cycle). The appropriate dose of J591-Ac$^{225}$ can be determined in a standard phase 1 trial format in which escalating doses of J591-Ac$^{225}$ are combined with the stated dose of PSMA-617-$^{177}$Lu above until an MTD is determined.

Alternatively, the $^{177}$Lu can be targeted by the Ab and Ac$^{225}$ by PSMA-617. In this case, the latter is dosed at 100 kbq/kg, and the the Ab J591 is dosed at J591-$^{177}$Lu 120-140 mCi total in a 2 week cycle. Another possible dose range of J591-$^{177}$Lu is from 100-160 mCi total in a 2 week cycle.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for treating prostate cancer in a subject, the method comprising co-administering to a subject in need thereof, a therapeutically effective amount of J591-Ac$^{225}$ and a therapeutically effective amount of a PSMA ligand/inhibitor wherein the PSMA ligand/inhibitor is a PSMA-Lu$^{177}$ peptide.

2. The method of claim 1, wherein the PSMA-Lu$^{177}$ peptide is PSMA I&T-Lu$^{177}$ or PSMA 617-Lu$^{177}$.

3. The method of claim 1, wherein the J591-Ac$^{225}$ and PSMA-L$^{177}$ peptide are administered in separate compositions.

4. The method of claim 3, wherein the separate compositions are administered to the subject by injection.

5. The method of claim 3, wherein the separate compositions are co-administered via simultaneous administration, sequential administration, continuous administration, or a combination thereof to the subject.

6. The method of claim 5, wherein the separate compositions are administered in a 2 week cycle.

7. The method of claim 1, wherein J591-Ac$^{225}$ and PSMA ligand/inhibitor are co-administered to the subject to allow for J591-Ac$^{225}$ and PSMA ligand/inhibitor to be dosed at about 25% to about 100% of their respective maximum tolerated doses.

8. The method of claim 7, wherein the PSMA ligand/inhibitor is a PSMA-Lu$^{177}$ peptide.

9. The method of claim 8, wherein the PSMA-Lu$^{177}$ peptide is PSMA I&T-Lu$^{177}$ or PSMA 617-Lu$^{177}$.

10. A combination therapeutic comprising: a therapeutically effective amount of J591-Ac$^{225}$ and a therapeutically effective amount of a PSMA ligand/inhibitor wherein the PSMA ligand/inhibitor is a PSMA-Lu$^{177}$ peptide.

11. The combination therapeutic of claim 10, wherein the PSMA-Lu$^{177}$ peptide is PSMA 617-Lu$^{177}$ or PSMA I&T-Lu$^{177}$.

12. The combination therapeutic of claim 10, wherein the J591-Ac$^{225}$ and the PSMA ligand/inhibitor are in the same or in separate compositions.

13. The combination therapeutic of claim 12, wherein the J591-Ac$^{225}$ and the PSMA ligand/inhibitor are in separate compositions.

14. The combination therapeutic of claim 13, wherein the separate compositions are formulated for injection to a subject.

15. The combination therapeutic of claim 13, wherein the separate compositions are formulated for co-administration via simultaneous administration, sequential administration, continuous administration, or a combination thereof to a subject.

16. The combination therapeutic of claim 13, wherein the separate compositions are administered to a subject in a 2 week cycle.

17. The combination therapeutic of claim 10, wherein the combination therapeutic is formulated for administration to a subject to deliver the J591-$Ac^{225}$ and PSMA ligand/inhibitor peptide at a dose of about 25% to about 100% of their respective maximum tolerated doses.

18. The combination therapeutic of claim 17, wherein the PSMA ligand/inhibitor is a PSMA-$Lu^{177}$ peptide.

19. The combination therapeutic of claim 18, wherein the PSMA-$Lu^{177}$ peptide is PSMA 617-$Lu^{177}$ or PSMA I&T-$Lu^{177}$.

\* \* \* \* \*

UNITED STATES PATENT AND TRADEMARK OFFICE
CERTIFICATE OF CORRECTION

PATENT NO. : 12,285,503 B2
APPLICATION NO. : 18/363369
DATED : April 29, 2025
INVENTOR(S) : Neil H. Bander It is certified that error appears in the above-identified patent and that said Letters Patent is hereby corrected as shown below:

In the Claims

In Claim 3, Column 20, Line 36, delete "PSMA-L$^{177}$" and insert --PSMA-Lu$^{177}$--;

In Claim 7, Column 20, Lines 46-47, delete "PSMA ligand/inhibitor" and insert --PSMA-Lu$^{177}$ peptide--;

In Claim 7, Column 20, Line 48, delete "PSMA ligand/inhibitor" and insert --PSMA-Lu$^{177}$ peptide--.

Signed and Sealed this
Twenty-second Day of July, 2025

Coke Morgan Stewart
*Acting Director of the United States Patent and Trademark Office*